US011565165B2

(12) United States Patent
Nakashima et al.

(10) Patent No.: US 11,565,165 B2
(45) Date of Patent: Jan. 31, 2023

(54) WALKING TRAINING SYSTEM, NON-TRANSITORY STORAGE MEDIUM STORING CONTROL PROGRAM FOR WALKING TRAINING SYSTEM AND CONTROL METHOD FOR WALKING TRAINING SYSTEM

(71) Applicant: TOYOTA JIDOSHA KABUSHIKI KAISHA, Toyota (JP)

(72) Inventors: Issei Nakashima, Toyota (JP); Nagisa Tanaka, Toyota (JP); Eiichi Saitoh, Nagoya (JP); Akihiro Saito, Tokyo (JP); Satoshi Hirano, Nagoya (JP); Shigeo Tanabe, Toyoake (JP); Takuma Ii, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 336 days.

(21) Appl. No.: 16/885,855

(22) Filed: May 28, 2020

(65) Prior Publication Data

US 2020/0384342 A1    Dec. 10, 2020

(30) Foreign Application Priority Data

Jun. 7, 2019   (JP) .............................. JP2019-106942

(51) Int. Cl.
*A61B 5/11* (2006.01)
*A63B 71/06* (2006.01)
(Continued)

(52) U.S. Cl.
CPC .......... *A63B 71/0622* (2013.01); *A61B 5/112* (2013.01); *A61B 5/1128* (2013.01); *A61B 5/742* (2013.01); *A61H 1/024* (2013.01); *A61H 1/0262* (2013.01); *A61H 3/008* (2013.01); *A63B 22/02* (2013.01); *A63B 24/0062* (2013.01); *G06V 40/25* (2022.01); *G09B 19/003* (2013.01);
(Continued)

(58) Field of Classification Search
None
See application file for complete search history.

(56) References Cited

U.S. PATENT DOCUMENTS

2012/0086793 A1    4/2012  Anabuki
2015/0325004 A1    11/2015 Utsunomiya et al.
(Continued)

FOREIGN PATENT DOCUMENTS

EP    3 142 095 A1    3/2017
JP    2011-019669 A   2/2011
(Continued)

*Primary Examiner* — Eileen M Adams
(74) *Attorney, Agent, or Firm* — Oliff PLC

(57) ABSTRACT

A walking training system includes a treadmill configured to prompt a trainee to walk, a display device installed such that the trainee views the display device while walking on the treadmill, a camera configured to image the trainee at an angle of view at which a gait of the trainee is recognizable, a calculation unit configured to calculate a tilt of a body core of the walking trainee based on an image captured by the camera, and a display control unit configured to control the display device to display a body core line associated with the tilt, and an index indicating at least an end of a permissible range of a deflection of the body core line.

9 Claims, 8 Drawing Sheets

(51) Int. Cl.
- *A61H 3/00* (2006.01)
- *A61H 1/02* (2006.01)
- *A63B 24/00* (2006.01)
- *A63B 22/02* (2006.01)
- *G06V 40/20* (2022.01)
- *A61B 5/00* (2006.01)
- *G09B 19/00* (2006.01)

(52) U.S. Cl.
CPC ... *A63B 2071/0652* (2013.01); *A63B 2220/05* (2013.01); *A63B 2220/806* (2013.01)

(56) References Cited

U.S. PATENT DOCUMENTS

| | | | |
|---|---|---|---|
| 2016/0051859 A1* | 2/2016 | Nakashima | A63B 21/4011 482/4 |
| 2017/0065849 A1* | 3/2017 | Konishi | G09B 19/003 |

FOREIGN PATENT DOCUMENTS

| | | |
|---|---|---|
| JP | 2012-081089 A | 4/2012 |
| JP | 2013-066696 A | 4/2013 |
| JP | 2015-042241 A | 3/2015 |
| JP | 2016-154647 A | 9/2016 |
| JP | 2016-179048 A | 10/2016 |
| JP | 2017-099788 A | 6/2017 |
| JP | 6406187 B2 | 10/2018 |

\* cited by examiner

WALKING TRAINING SYSTEM, NON-TRANSITORY STORAGE MEDIUM STORING CONTROL PROGRAM FOR WALKING TRAINING SYSTEM AND CONTROL METHOD FOR WALKING TRAINING SYSTEM

INCORPORATION BY REFERENCE

The disclosure of Japanese Patent Application No. 2019-106942 filed on Jun. 7, 2019 including the specification, drawings and abstract is incorporated herein by reference in its entirety.

BACKGROUND

1. Technical Field

The disclosure relates to a walking training system, a non-transitory storage medium storing a control program for the walking training system, and a control method for the walking training system.

2. Description of Related Art

There is known a technology that involves imaging a subject of posture evaluation through a half-silvered mirror, calculating a centroidal line of a human body or the like, and displaying a computer graphics (CG) image of the centroidal line on the half-silvered mirror (see, for example, Japanese Unexamined Patent Application Publication No. 2012-81089 (JP 2012-81089 A)).

SUMMARY

When walking training is executed for a paralysis patient with a mobility difference between right and left legs because he/she suffers from hemiplegia or wears a prosthesis, the paralysis patient has difficulty in intuitively grasping the degree of tilt of his/her body relative to a permissible body deflection range during the execution of the walking training.

The disclosure provides a walking training system and the like in which a trainee who undergoes walking training can intuitively grasp the degree of tilt of his/her body relative to a permissible body deflection range.

A first aspect of the disclosure relates to a walking training system. The walking training system includes a treadmill, a display device, a camera, a calculation unit, and a display control unit. The treadmill is configured to prompt a trainee to walk. The display device is installed such that the trainee views the display device while walking on the treadmill. The camera is configured to image the trainee at an angle of view at which a gait of the trainee is recognizable. The calculation unit is configured to calculate a tilt of a body core of the walking trainee based on an image captured by the camera. The display control unit is configured to control the display device to display a body core line associated with the tilt, and an index indicating at least an end of a permissible range of a deflection of the body core line. Since the display device displays both the body core line and the permissible deflection range, the trainee can intuitively grasp whether his/her current tilt falls beyond the permissible range. If the tilt does not fall beyond the permissible range, the trainee can intuitively grasp the degree of allowance relative to the deflection range.

In the walking training system of the aspect described above, the display control unit may be configured to cause the display device to display the body core line and the index such that the body core line and the index are superimposed on the captured image of the trainee. When graphics of the body core line and the index are superimposed on a video of the trainee, the trainee can grasp his/her gait more intuitively. In the walking training system of the aspect described above, the display control unit may be configured to render the body core line with a base point being defined near a heel of an affected leg of the trainee. The body core tilt is calculated based on parts except limbs. Therefore, the body core line may originally be superimposed on a trunk of the trainee. For the trainee who undergoes walking training, the body core tilt is mainly caused by the condition of the affected leg. Therefore, when the body core line is rendered with the base point being defined near the heel of the affected leg, the body core line matches well with sensation of the trainee. Further, the visibility is improved because a large body core line can be rendered. In the walking training system of the aspect described above, the display control unit may be configured to render the range as a sector having a pivot at the base point. When the body core line swings relative to the sector, the trainee can grasp his/her gait more intuitively.

The walking training system of the aspect described above may include an evaluation unit configured to evaluate the gait. The display control unit may be configured to display an object based on an evaluation result from the evaluation unit. By visualizing the evaluation unit, it can be expected that the trainee has a higher motivation for the walking training. In the walking training system of the aspect described above, the display control unit may be configured to display an indicator serving as the object included in the sector such that the indicator increases or decreases based on the evaluation unit. In the walking training system of the aspect described above, the display control unit may be configured to display an event indicating that a level is cleared when the indicator is displayed in a full amount. By executing the display described above, a gaming feature can be provided to the walking training, and the trainee can enjoy the walking training more.

In the walking training system of the aspect described above, the display control unit may be configured such that, when the evaluation unit detects inappropriateness of the gait, the object indicating the inappropriateness is displayed near the base point of the body core line. When the object is displayed near the heel of the affected leg that is a main cause of the inappropriateness of the gait, the trainee can grasp more intuitively that the gait is inappropriate.

A second aspect of the disclosure relates to a non-transitory storage medium storing a control program for a walking training system. The walking training system includes a treadmill, a display device, and a camera. The treadmill is configured to prompt a trainee to walk. The display device is installed such that the trainee views the display device while walking on the treadmill. The camera is configured to image the trainee at an angle of view at which a gait of the trainee is recognizable. The non-transitory storage medium stores instructions that are executable by one or more processors and that cause the one or more processors to perform the following functions. The functions include calculating a tilt of a body core of the walking trainee based on an image captured by the camera, and causing the display device to display a body core line associated with the tilt, and an index indicating at least an end of a permissible range of a deflection of the body core line.

A third aspect of the disclosure relates to a control method for a walking training system. The walking training system includes a treadmill, a display device, and a camera. The treadmill is configured to prompt a trainee to walk. The display device is installed such that the trainee views the display device while walking on the treadmill. The camera is configured to image the trainee at an angle of view at which a gait of the trainee is recognizable. The control method includes calculating a tilt of a body core of the walking trainee based on an image captured by the camera; and causing the display device to display a body core line associated with the tilt, and an index indicating at least an end of a permissible range of a deflection of the body core line.

According to the disclosure, the trainee can intuitively grasp the degree of tilt of his/her body relative to the permissible body deflection range during the walking training.

BRIEF DESCRIPTION OF THE DRAWINGS

Features, advantages, and technical and industrial significance of exemplary embodiments will be described below with reference to the accompanying drawings, in which like signs denote like elements, and wherein.

DETAILED DESCRIPTION OF EMBODIMENTS

An embodiment of the disclosure is described below. The disclosure according to the claims is not limited to the embodiment described below. All constituent elements described in the embodiment are not essential to solve the problem.

Figure 1:
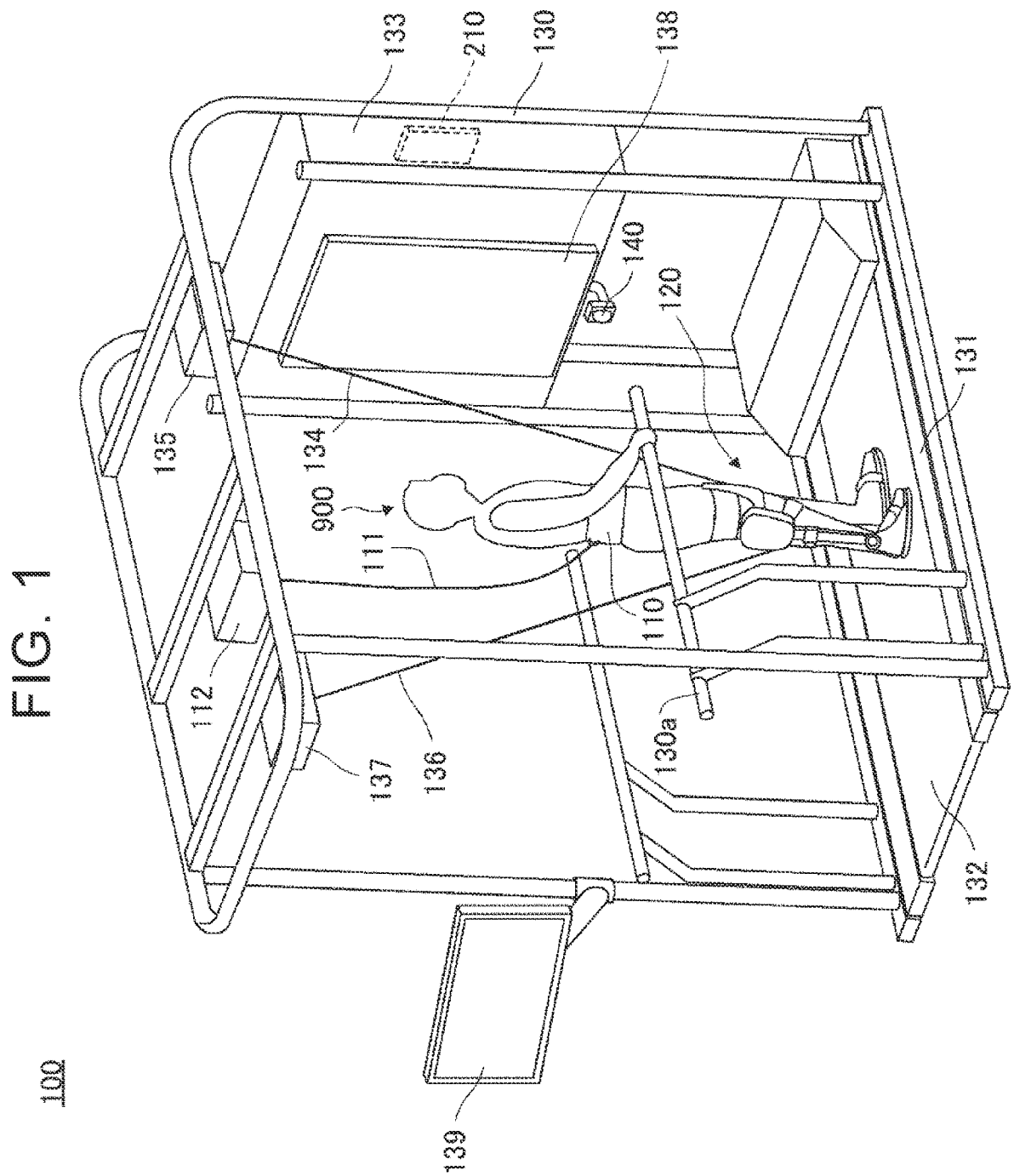
FIG. 1 is a schematic perspective view of a walking training apparatus according to an embodiment.

FIG. 1 is a schematic perspective view of a walking training apparatus 100 according to this embodiment. The walking training apparatus 100 is an example of a walking training system. A trainee 900 undergoes walking training by using the walking training apparatus 100. The trainee 900 is a hemiplegia patient suffering from paralysis in one leg. The walking training apparatus 100 mainly includes a control panel 133, a treadmill 131, and a walking assistance device 120. The control panel 133 is attached to a frame 130 that constitutes the entire skeleton. The trainee 900 walks on the treadmill 131. The walking assistance device 120 is attached to an affected leg of the trainee 900, which is a paralytic leg.

The frame 130 is provided upright on the treadmill 131 installed on a floor. The treadmill 131 rotates a ring-shaped belt 132 by using a motor (not illustrated). The treadmill 131 prompts the trainee 900 to walk. The trainee 900 who undergoes walking training stands on the belt 132, and attempts to walk in synchronization with movement of the belt 132.

The frame 130 supports the control panel 133, a training monitor 138, and the like. The control panel 133 houses an overall control unit 210 configured to control motors and sensors. For example, the training monitor 138 is a liquid crystal display panel configured to display progress of training and the like for the trainee 900. That is, the training monitor 138 is a display unit, and is installed such that the trainee 900 can view the training monitor 138 while walking on the belt 132 of the treadmill 131. The frame 130 supports a front tension unit 135 near the front of an area over the head of the trainee 900, a harness tension unit 112 near the area over the head, and a rear tension unit 137 near the rear of the area over the head. The frame 130 includes handrails 130a to be gripped by the trainee 900.

A camera unit 140 images the trainee 900 at an angle of view at which a gait of the trainee is recognizable. The camera unit 140 of this embodiment includes a set of a lens and an imaging device to achieve an angle of view at which the camera unit 140 can capture the entire body of the trainee 900 standing on the belt 132, including his/her the head. For example, the imaging device is a complementary metal-oxide semiconductor (CMOS) image sensor, and converts an optical image formed on an imaging plane into an image signal. The camera unit 140 is installed near the training monitor 138 to face the trainee 900.

A front wire 134 has one end coupled to a reeling mechanism of the front tension unit 135, and the other end coupled to the walking assistance device 120. The reeling mechanism of the front tension unit 135 reels or unreels the front wire 134 in response to a motion of the affected leg by turning ON or OFF a motor (not illustrated). Similarly, a rear wire 136 has one end coupled to a reeling mechanism of the rear tension unit 137, and the other end coupled to the walking assistance device 120. The reeling mechanism of the rear tension unit 137 reels or unreels the rear wire 136 in response to a motion of the affected leg by turning ON or OFF a motor (not illustrated). Through the cooperative operation of the front tension unit 135 and the rear tension unit 137, a load of the walking assistance device 120 is balanced so as not to burden the affected leg. Further, the swing of the affected leg is assisted depending on a set level.

For example, an operator who is a training assistant sets a high assistance level for a trainee suffering from severe paralysis. When the high assistance level is set, the front tension unit 135 reels the front wire 134 with a relatively great force in synchronization with a timing to swing the affected leg. If the training proceeds and no assistance is needed, the operator sets a minimum assistance level. When the minimum assistance level is set, the front tension unit 135 reels the front wire 134 with a force for canceling the self-weight of the walking assistance device 120 in synchronization with a timing to swing the affected leg.

The walking training apparatus 100 includes a safety device having an attachment 110, a harness wire 111, and the harness tension unit 112 as main components. The attachment 110 is a belt to be attached around the waist of the trainee 900, and is fixed to the waist with, for example, a hook-and-loop fastener. The harness wire 111 has one end coupled to the attachment 110, and the other end coupled to a reeling mechanism of the harness tension unit 112. The reeling mechanism of the harness tension unit 112 reels or unreels the harness wire 111 by turning ON or OFF a motor (not illustrated). The safety device having this structure is configured such that, when the trainee 900 loses his/her balance significantly, the harness wire 111 is reeled and the attachment 110 supports the upper body of the trainee 900 in response to an instruction from the overall control unit 210 that detects the motion of the trainee 900.

A management monitor 139 is a display/input device attached to the frame 130 and mainly used by the operator for monitoring and operation. For example, the management monitor 139 is a liquid crystal display panel, and is provided with a touch panel on its surface. The management monitor 139 displays various menu items related to training settings, various parameters during the training, and results of the training.

Figure 2:
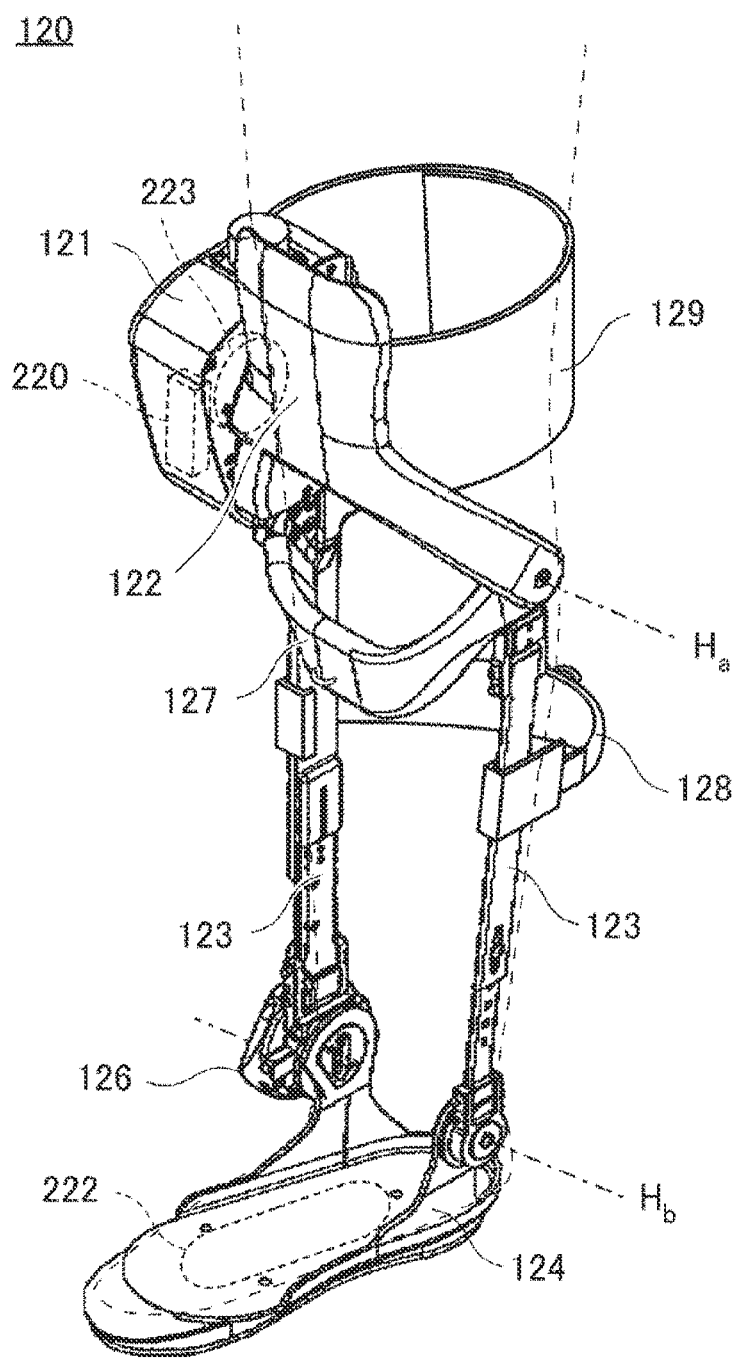
FIG. 2 is a schematic perspective view of a walking assistance device.

The walking assistance device 120 is attached to the affected leg of the trainee 900, and assists walking of the trainee 900 by reducing loads caused by stretching and bending a knee joint of the affected leg. FIG. 2 is a schematic perspective view of the walking assistance device 120. The walking assistance device 120 mainly includes a control unit 121, a plurality of frames, and a load sensor 222. The frames support respective parts of the affected leg. The load sensor 222 detects a load on a sole.

The control unit 121 includes an assistance control unit 220 and a motor (not illustrated). The assistance control unit 220 controls the walking assistance device 120. The motor generates a driving force for assisting stretching and bending motions of the knee joint. The frames that support respective parts of the affected leg include an upper thigh frame 122, a lower thigh frame 123, a foot frame 124, a front coupling frame 127, and a rear coupling frame 128. The lower thigh frame 123 is pivotably coupled to the upper thigh frame 122. The foot frame 124 is pivotably coupled to the lower thigh frame 123. The front wire 134 is coupled to the front coupling frame 127. The rear wire 136 is coupled to the rear coupling frame 128. The front coupling frame 127 extends in a lateral direction in front of an upper thigh, and both ends of the front coupling frame 127 are connected to the upper thigh frame 122. The rear coupling frame 128 extends in the lateral direction behind a lower thigh, and both ends of the rear coupling frame 128 are connected to the lower thigh frame 123 extending in a vertical direction.

The upper thigh frame 122 and the lower thigh frame 123 pivot relative to each other about an illustrated hinge axis $H_a$. The motor of the control unit 121 rotates in response to an instruction from the assistance control unit 220 to apply a force so that the upper thigh frame 122 and the lower thigh frame 123 are opened or closed relative to each other about the hinge axis $H_a$. An angle sensor 223 housed in the control unit 121 is, for example, a rotary encoder, and detects an angle between the upper thigh frame 122 and the lower thigh frame 123 about the hinge axis $H_a$. The lower thigh frame 123 and the foot frame 124 pivot relative to each other about an illustrated hinge axis $H_b$. An adjustment mechanism 126 preadjusts an angle range in which the lower thigh frame 123 and the foot frame 124 pivot relative to each other.

The upper thigh frame 122 includes an upper thigh belt 129. The upper thigh belt 129 is provided integrally with the upper thigh frame, and is attached around the upper thigh of the affected leg to fix the upper thigh frame 122 to the upper thigh. The upper thigh belt 129 restrains the entire walking assistance device 120 from being misaligned from the leg of the trainee 900.

The load sensor 222 is embedded in the foot frame 124. The load sensor 222 detects the magnitude and distribution of a vertical load on the sole of the trainee 900. For example, the load sensor 222 is a load detection sheet of a resistance variation detection type, in which electrodes are arranged in a matrix.

Figure 3:
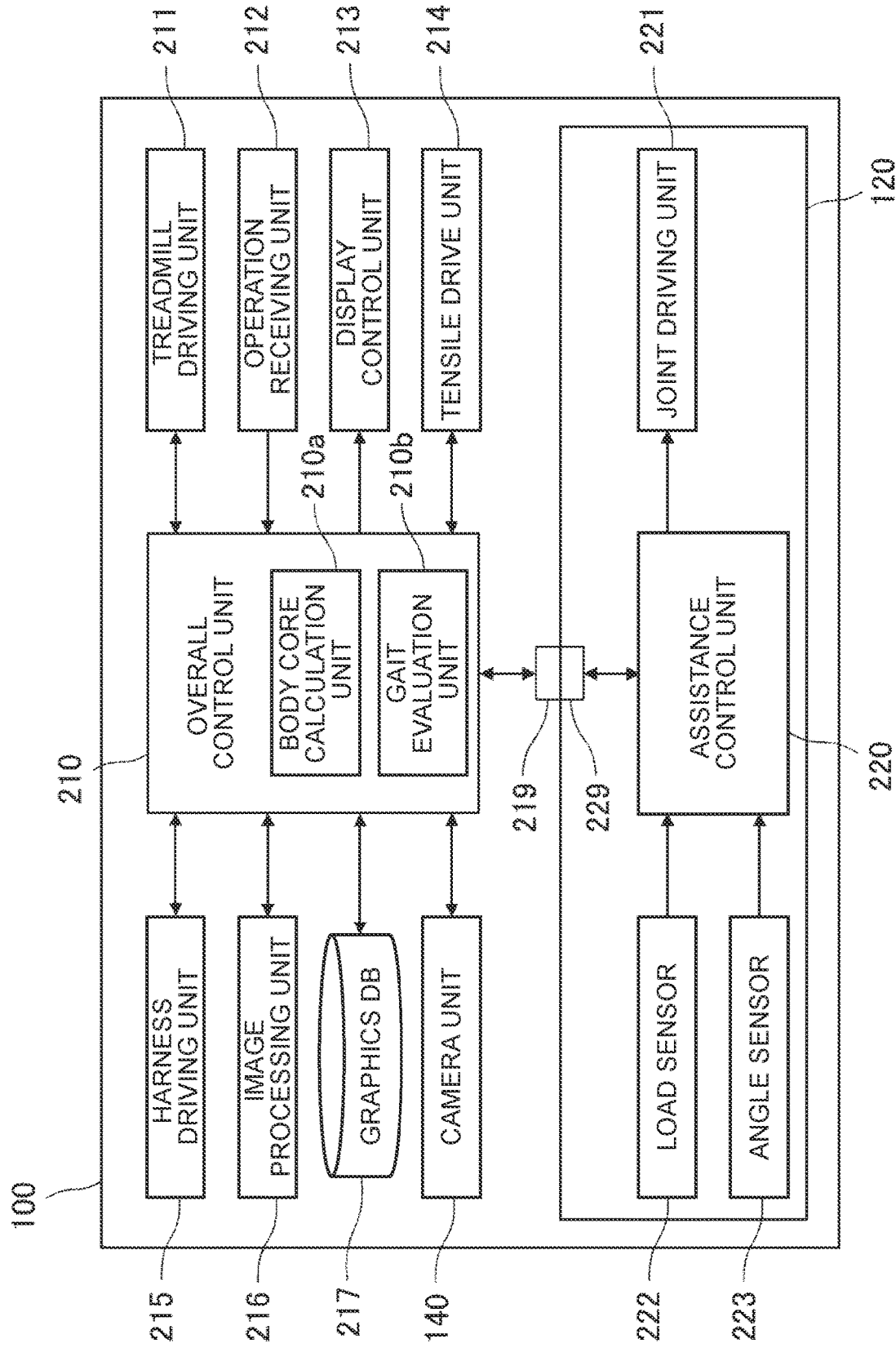
FIG. 3 is a diagram illustrating the system configuration of the walking training apparatus.

Next, the system configuration of the walking training apparatus 100 is described. FIG. 3 is a system configuration diagram of the walking training apparatus 100. For example, the overall control unit 210 is a microprocessor (MPU), and controls the entire apparatus by executing a control program read from a system memory. A treadmill driving unit 211 includes a motor for rotating the belt 132, and a drive circuit for the motor. The overall control unit 210 controls the rotation of the belt 132 by transmitting a drive signal to the treadmill driving unit 211. For example, the rotation speed of the belt 132 is adjusted depending on a set training level.

An operation receiving unit 212 receives an input operation from the trainee 900 or the operator, and transmits an operation signal to the overall control unit 210. The trainee 900 or the operator operates operation buttons of the operation receiving unit 212, a touch panel superimposed on the management monitor 139, or an attached remote control to give an instruction to turn ON or OFF the power or an instruction to start training, to input values related to settings, or to select a menu item.

A display control unit 213 generates a display video and displays the display video on the training monitor 138 or the management monitor 139 in response to a control signal from the overall control unit 210. For example, the display control unit 213 generates a video showing progress of training. Although details are described later, the display control unit 213 causes the training monitor 138 to display, as computer graphics (CG) images, a body core line associated with a body core tilt of the trainee 900 who undergoes walking training, and an index of a permissible range of a deflection of the body core line.

A tensile drive unit 214 includes a motor for pulling the front wire 134, a drive circuit for the motor, a motor for pulling the rear wire 136, and a drive circuit for the motor. The overall control unit 210 controls reeling of the front wire 134 and reeling of the rear wire 136 by transmitting drive signals to the tensile drive unit 214. In addition to the control on the reeling operations, the overall control unit 210 controls tensile forces of the respective wires by controlling driving torques of the motors. For example, the overall control unit 210 determines a timing when the affected leg is switched from a stance phase to a swing phase based on a detection result from the load sensor 222, and increases or reduces the tensile forces of the respective wires in synchronization with the timing, thereby assisting the swing of the affected leg.

A harness driving unit 215 includes a motor for pulling the harness wire 111, and a drive circuit for the motor. The overall control unit 210 controls reeling of the harness wire 111 and a tensile force of the harness wire 111 by transmitting a drive signal to the harness driving unit 215. For example, when the trainee 900 loses his/her balance significantly, the overall control unit 210 reels the harness wire 111 by a predetermined amount to restrain the trainee from falling down.

An image processing unit 216 generates image data by performing image processing on an image signal received from the camera unit 140 in response to a control signal from the overall control unit 210. The image processing unit 216 can also analyze a specific image by performing image processing on an image signal received from the camera unit 140 in response to an instruction from the overall control unit 210. For example, the positions of both shoulders and the position of a hip joint can be detected based on information on an extracted edge. The positional information serves as input information for body core calculation described later. Similarly, the position near a heel of the affected leg can be detected in the acquired image. The information is used for determining a position where a CG image is rendered.

The camera unit 140 repeats an imaging operation and outputs an image signal to the image processing unit 216 in response to a control signal from the overall control unit 210. A graphics DB 217 stores CG materials to be displayed on the training monitor 138 or the management monitor 139. The overall control unit 210 reads, from the graphics DB 217, CG materials to be displayed on the monitors, and transfers the CG materials to the display control unit 213. The display control unit 213 generates a display video by placing the received CG materials at predetermined positions through magnification or rotation processing on the CG materials.

The overall control unit 210 also serves as a function executing unit configured to execute various types of control and various types of calculation related to control. A body core calculation unit 210a calculates a body core tilt of the walking trainee 900 in response to a result of analysis performed by the image processing unit 216 on a trainee image captured by the camera unit 140. Specifically, a body core in the image is determined by connecting reference positions of a main skeleton, such as the positions of both shoulders and the position of the hip joint that are analyzed by the image processing unit 216, and an angle between an extending direction of the body core and an axis normal to a walking plane is calculated as a tilt angle. A gait evaluation unit 210b evaluates a gait of the trainee 900 by using the body core tilt calculated by the body core calculation unit 210a. The gait evaluation unit 210b may make evaluation in consideration of, for example, dragging, stumbling, and gripping of the handrail 130a that are detected based on image analysis performed by the image processing unit 216 or outputs from sensors such as the load sensor 222 and a distance sensor. The distance sensor may be a depth sensor configured to project pattern light onto a measurement target and acquire a distance between a plurality of points based on the degree of distortion.

As described above, the walking assistance device 120 is attached to the affected leg of the trainee 900. The walking training apparatus 100 includes a communication connection interface (IF) 219 connected to the overall control unit 210 to give instructions to the walking assistance device 120 and receive sensor information. The walking assistance device 120 is provided with a communication connection IF 229 connected to the communication connection IF 219 by wire or wireless. The communication connection IF 229 is connected to the assistance control unit 220 of the walking assistance device 120. Each of the communication connection IFs 219 and 229 is a communication interface such as a wireless local area network (LAN) conforming to a communication standard.

For example, the assistance control unit 220 is an MPU, and controls the walking assistance device 120 by executing a control program provided from the overall control unit 210. The assistance control unit 220 notifies the overall control unit 210 of the condition of the walking assistance device 120 via the communication connection IFs 219 and 229. The assistance control unit 220 starts or stops the walking assistance device 120 in response to an instruction from the overall control unit 210.

A joint driving unit 221 includes the motor of the control unit 121 and a drive circuit for the motor. The assistance control unit 220 transmits a drive signal to the joint driving unit 221 to apply a force so that the upper thigh frame 122 and the lower thigh frame 123 are opened or closed relative to each other about the hinge axis $H_a$. This operation assists stretching and bending motions of the knee, and restrains unintended bending on the knee. As described above, the load sensor 222 detects the magnitude and distribution of a vertical load on the sole of the trainee 900, and transmits a detection signal to the assistance control unit 220.

The assistance control unit 220 receives and analyzes the detection signal to determine whether the affected leg is in a swing phase or a stance phase or to estimate switching between the swing phase and the stance phase. As described above, the angle sensor 223 detects an angle between the upper thigh frame 122 and the lower thigh frame 123 about the hinge axis $H_a$, and transmits a detection signal to the assistance control unit 220. The assistance control unit 220 receives the detection signal, and calculates an open angle of the knee joint.

The walking training apparatus 100 of this embodiment employs a gaming feature in execution of training so that the trainee 900 can enjoy walking training. Specifically, in order that the trainee can achieve each target condition set based on a training plan, a training program gives a high score to the execution of the training if the trainee walks while keeping a predetermined gait without unsteadiness. Moreover, score information is updated with a dynamic and real-time visual effect depending on progress of the training. Description is given of several display examples on the training monitor 138 during the execution of the training.

Figure 4:
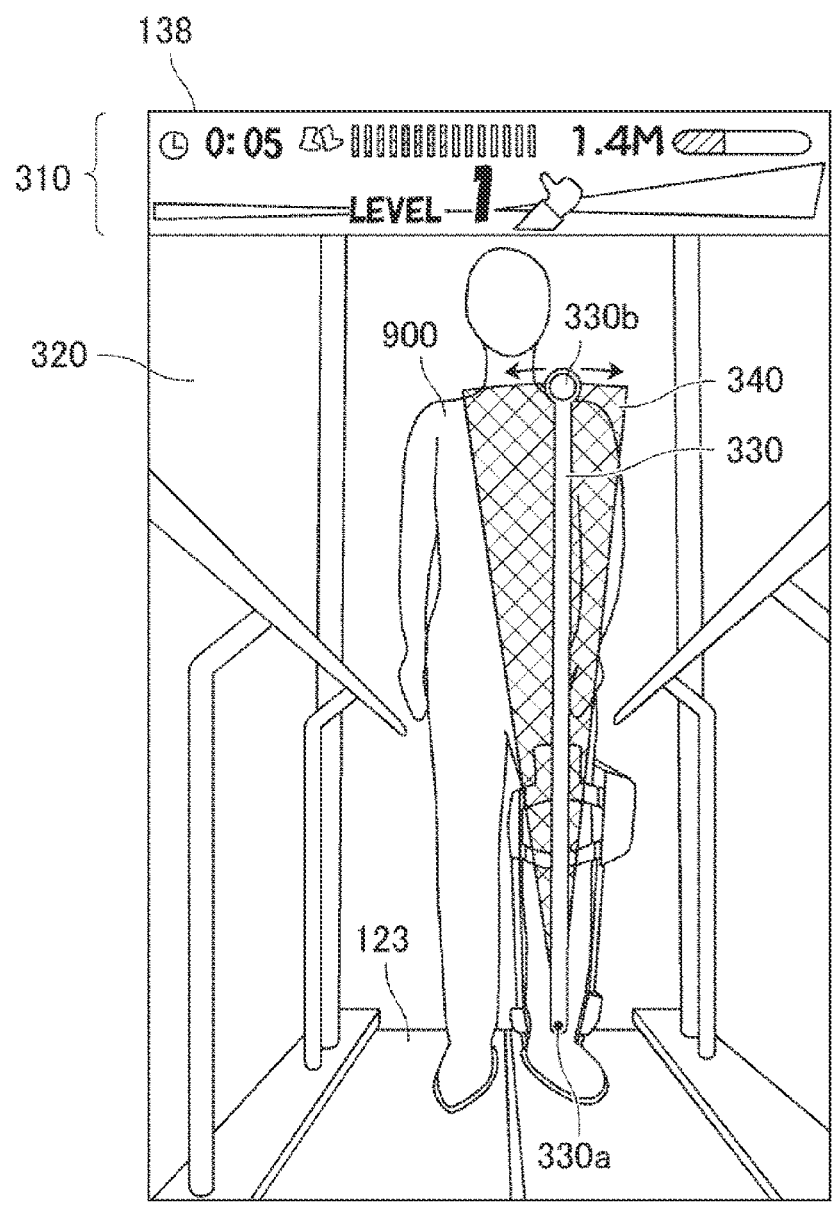
FIG. 4 is an illustration of a display example of a case where a gait is normal.

FIG. 4 illustrates a display example on the training monitor 138 in a case where the gait of the trainee 900 is normal. A status field 310 is provided at an uppermost part of the training monitor 138. Status information in the execution of the training is displayed in the status field 310. The status information includes a duration, a walking distance, a training level, a score indicator, and the like. The duration is a time from the start of execution, and is measured by using a timer (not illustrated). The walking distance is measured based on a cumulative rotation amount of the belt 132 rotated by the treadmill driving unit 211. The training level indicates difficulty in the execution of the training, and is updated every time the trainee satisfies a preset criterion. The difficulty in the execution of the training is determined based on the rotation speed of the belt 132 and the assistance amount of the walking assistance device 120. At the start of training, the training level is set by the training assistant who is a therapist or the like in conjunction with the condition of the trainee 900. The score indicator increases or decreases based on an increase or decrease of earned points described later.

A camera image 320 is displayed in a field other than the status field 310 in the training monitor 138. The camera image 320 is an image of the entire trainee 900 photographed by the camera unit 140, and is displayed as a real-time video of, for example, 60 fps. The trainee 900 can view himself/herself as the real-time video during the execution of the training. Since the trainee 900 faces the training monitor 138, the camera image 320 is preferably a mirror image as in the illustration from the viewpoint of visibility.

A body core line 330 and a deflection index 340 are superimposed on the camera image 320 as CG images. The body core line 330 is associated with the body core tilt calculated by the body core calculation unit 210a. The deflection index 340 indicates a permissible range of a deflection of the body core line 330. In this embodiment, the body core line 330 is represented by a CG image of a straight pole extending to the vicinity of a shoulder from a base point 330*a* near the heel of the affected leg of the trainee 900. An end point 330*b* near the shoulder is slightly decorated so that the deflection of the body core can be viewed easily.

When the trainee 900 stands upright on the belt 132, the body core line 330 from the base point 330*a* to the end point 330*b* is rendered perpendicular to the surface of the belt 132. When the body core of the trainee 900 swings along with walking, the body core line 330 swings about the base point 330*a* depending on a tilt angle of the body core. Since the base point 330*a* is defined at a position near the heel of the affected leg, the entire body core line 330 moves along with the motion of the affected leg (stance or swing phase). For the trainee 900 who undergoes the walking training, an inappropriate body core tilt is mainly caused by the condition of the affected leg. Therefore, when the body core line 330 is rendered so that the base point is defined at the position near the heel of the affected leg, the body core line 330 matches well with sensation in perception of causality. When the body core line 330 is rendered to extend from the vicinity of the heel to the vicinity of the shoulder, the body core line 330 is a relatively large object in the display field of the training monitor 138. Therefore, the visibility is improved.

The deflection index 340 is rendered as a sector having a pivot at the base point 330*a* of the body core line 330. The arc of the sector is rendered along a swing direction of the end point 330*b* of the body core line 330. The central angle of the sector is determined based on the permissible range of the deflection of the body core line 330. For example, the deflection index 340 is preferably rendered semitransparent with a light color. When the deflection index 340 is rendered semitransparent, the body of the trainee 900 is not widely hidden behind the deflection index 340. Therefore, the trainee 900 can check his/her condition more correctly. The permissible deflection range is preset for each training level. A wide permissible deflection range is set while the training level is low. The permissible deflection range is set gradually smaller as the training level increases.

When the deflection index 340 is rendered as the sector and when the body core line 330 swinging along with the leg motion falls within the range of the sector, the trainee 900 can recognize that the gait is permissible in the execution of the training. Even if the trainee 900 does not gaze at the entire body core line 330, the trainee 900 can recognize whether the current body core tilt falls within the permissible range, for example, when the trainee 900 takes a glance as to whether the end point 330*b* is present on the arc of the sector. Such rendering is convenient to the trainee 900 who sees his/her feet or the assistant during the execution of the training. As described above, the body core line 330 and the deflection index 340 are rendered based on the calculation performed by the body core calculation unit 210*a*, and are recognized while being distinguished from the trainee 900.

Figure 5:
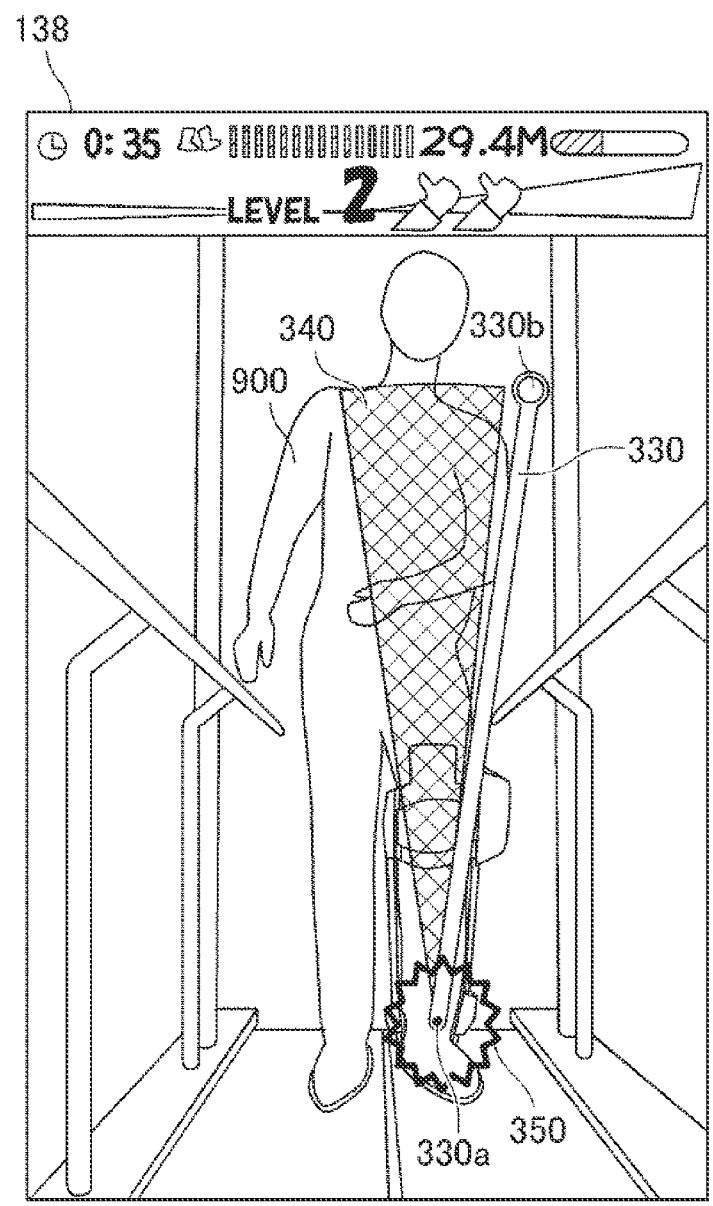
FIG. 5 is an illustration of a display example of a case where the gait is inappropriate.

FIG. 5 illustrates a display example on the training monitor 138 in a case where the gait of the trainee 900 is inappropriate. Although various types of inappropriateness are present about the gait of the trainee 900 that is evaluated by the gait evaluation unit 210*b*, an abnormal body core tilt is described as a representative example.

The gait evaluation unit 210*b* determines whether the body core tilt of the trainee 900 that is calculated by the body core calculation unit 210*a* falls within the set permissible deflection range. When the body core tilt falls out of the permissible deflection range, the gait evaluation unit 210*b* evaluates that the gait is inappropriate. When the inappropriateness is detected, an inappropriateness object 350 indicating the inappropriateness is displayed near the base point 330*a* of the body core line 330. In FIG. 5, the inappropriateness object 350 is represented by a graphical object that implies explosion. Different objects may be displayed depending on the degree or cause of inappropriateness. The inappropriateness object 350 may be represented by an animation. When the object is displayed near the heel of the affected leg that is a main cause of the inappropriateness of the gait, the trainee 900 can grasp more intuitively that the gait is inappropriate.

The body core line 330 is displayed while tilting about the base point 330*a* depending on the body core tilt of the trainee 900 that is calculated by the body core calculation unit 210*a*. Therefore, when the body core tilt falls out of the set permissible deflection range, the body core line 330 is rendered while tilting beyond the outer edge of the deflection index 340. That is, the end point 330*b* is rendered away from the arc of the deflection index 340. When the body core line 330 associated with the body core tilt of the trainee 900 and the index such as the deflection index 340 that prompts the trainee 900 to view the ends of the permissible range of the deflection of the body core line 330 are simultaneously displayed on the training monitor 138, the trainee 900 can easily recognize his/her condition. That is, the trainee 900 can intuitively grasp the degree of tilt of his/her body relative to the permissible body deflection range during the execution of the walking training though the trainee 900 has a mobility difference between right and left legs because he/she suffers from hemiplegia or wears the walking assistance device 120.

Figure 6:
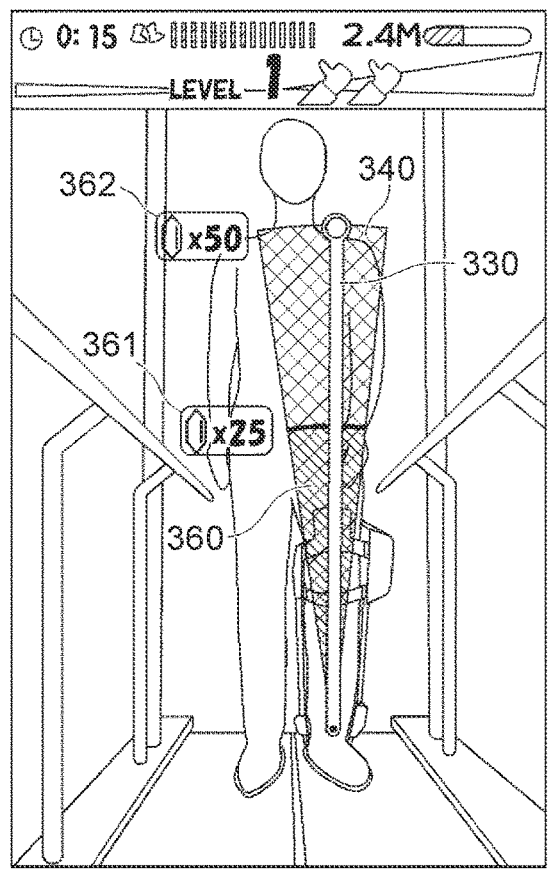
FIG. 6 is an illustration of a display example showing progress of execution of training.

The walking training apparatus 100 of this embodiment provides the gaming feature to the walking training. Display related to the gaming feature is described. FIG. 6 illustrates a display example showing progress of execution of training. In the display example of FIG. 5, the inappropriateness object 350 is displayed as an evaluation result from the gait evaluation unit 210*b*. In the display example of FIG. 6, the evaluation result from the gait evaluation unit 210*b* is converted into earned points and an object is displayed based on the earned points to provide the gaming feature.

Specifically, an achievement indicator 360 included in the sector of the deflection index 340 is displayed so as to increase or decrease depending on the evaluation result from the gait evaluation unit 210*b*. Further, a point index 361 is displayed adjacent to the achievement indicator 360 so that the degree of current achievement is recognizable at a glance. Still further, a clear index 362 is displayed near the top of the deflection index 340 so that points to be earned to clear a current level are recognizable. As in the illustration, the point index 361 and the clear index 362 are rendered, for example, by using icons and values indicating the points.

The earned points are increased when the body core line 330 falls within the range of the deflection index 340 continuously for a predetermined time (for example, 1 second). The achievement indicator 360 is expanded toward the arc of the deflection index 340. The earned points may also be increased based on other such evaluation points that the leg motion is periodic. The earned points are reduced when the body core line 330 falls out of the range of the deflection index 340. The achievement indicator 360 is shrunk toward the pivot of the deflection index 340. The earned points may also be reduced based on other such evaluation points that dragging is detected.

Figure 7:
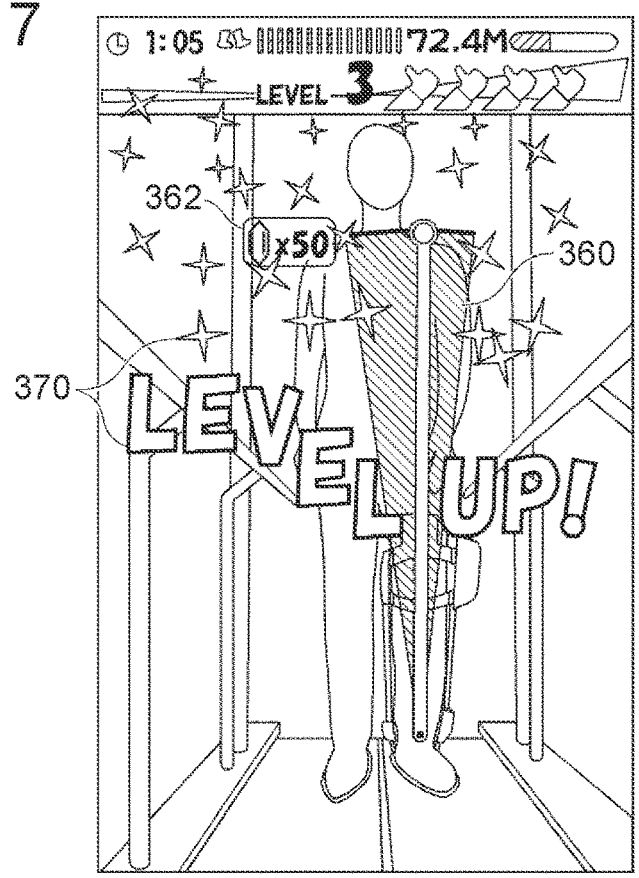
FIG. 7 is an illustration of a display example showing that an event is cleared in the execution of the training.

FIG. 7 illustrates a display example showing that an event is cleared in the execution of the training. When the earned points reach clear points, that is, the achievement indicator 360 is displayed in its full amount during the execution of the training, evaluation is made that a current level is cleared, and an event is displayed to indicate that the level is cleared. For example, the event is displayed by rendering an event object 370 including a character string "LEVEL UP!" that changes as an animation and crosses that represent glitter. By displaying the event in this manner, the gaming feature can be provided to the walking training, and the trainee 900 can enjoy the walking training more.

Figure 8:
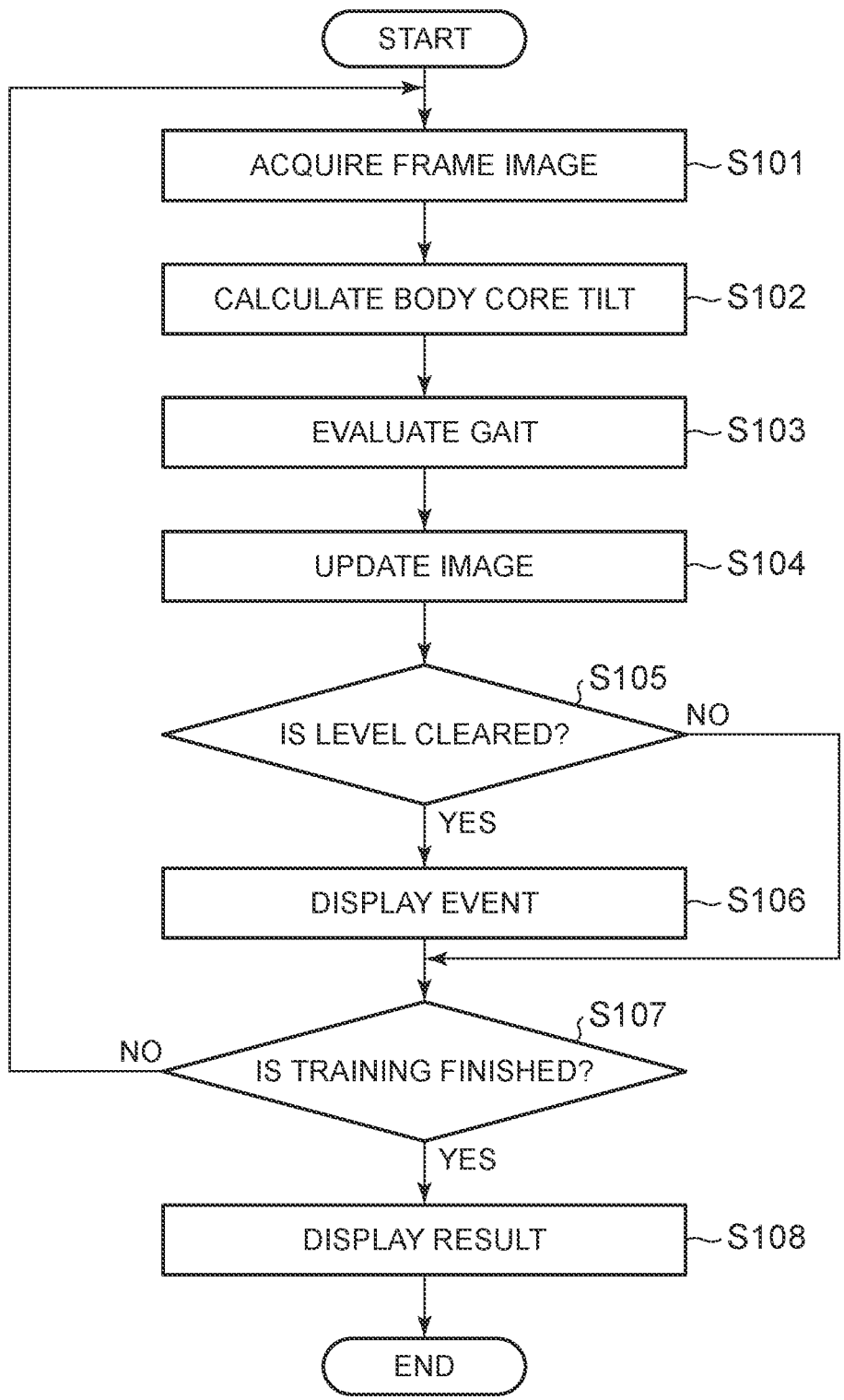
FIG. 8 is a diagram illustrating a flow of display processing in one execution of training.

Next, description is given of a flow of display processing in the execution of the training. FIG. 8 is a diagram illustrating a flow of display processing in one execution of the training. The illustrated flow is started in a state in which the training is started and the belt 132 starts to move.

In Step S101, the overall control unit 210 acquires a frame image showing the trainee 900 by causing the camera unit 140 to perform imaging processing. The image processing unit 216 receives the frame image output from the camera unit 140, performs image processing on the frame image, and performs image analysis to detect the positions of both shoulders and the position of the hip joint.

In Step S102, the body core calculation unit 210a receives the positions of both shoulders and the position of the hip joint that are detected by the image processing unit 216, and calculates a body core tilt of the trainee 900. In Step S103, the gait evaluation unit 210b receives the body core tilt calculated by the body core calculation unit 210a, and evaluates the gait of the trainee 900 by determining whether the tilt falls within the permissible deflection range.

In Step S104, the display control unit 213 adjusts the display video by superimposing, based on the calculated body core tilt, the body core line 330, the deflection index 340, and other display objects on the frame image of the trainee 900 subjected to the image processing by the image processing unit 216. The adjusted display video is transmitted to the training monitor 138, and the video displayed thus far is updated. The processing proceeds to Step S105, and the display control unit 213 checks whether the earned points reach the clear points. When the earned points reach the clear points, an event is displayed to indicate that the level is cleared (Step S106). Then, the processing proceeds to Step S107. When the earned points do not reach the clear points, the processing proceeds to Step S107 while skipping Step S106.

In Step S107, the overall control unit 210 determines whether the training is finished. For example, a duration, a walking distance, and achievement of a target level are preset as finish conditions. When the overall control unit 210 determines that the training is not finished, the processing returns to Step S101, and the training is continued. When the overall control unit 210 determines that the training is finished, the processing proceeds to Step S108. In Step S108, the display control unit 213 displays a result of the training. Examples of the result of the training include a walking distance, total earned points, an achieved level, and an evaluation comment. When the display control unit 213 displays the result, the overall control unit 210 terminates the series of processing steps.

Figure 9:
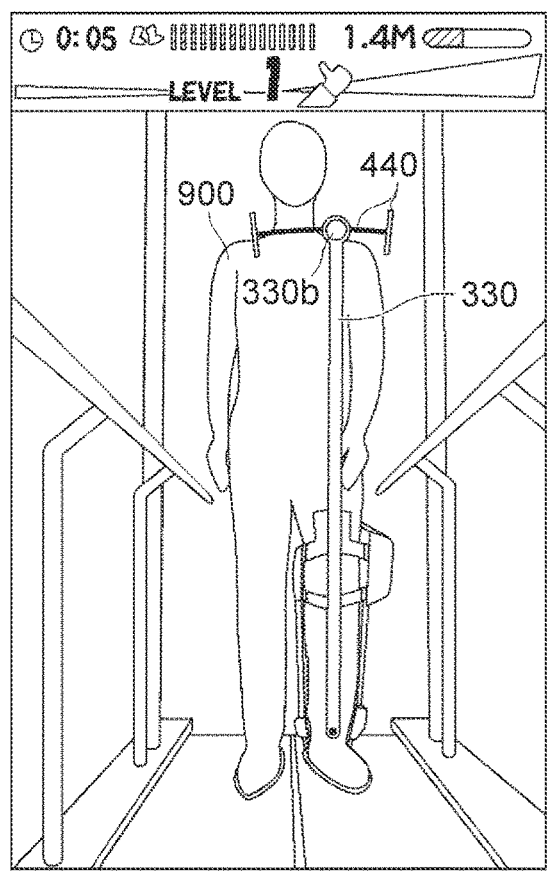
FIG. 9 is an illustration of another display example.

In the embodiment described above, the deflection index 340 is rendered as the sector having a pivot at the base point 330a of the body core line 330, but is not limited to the sector, and may be rendered variously. Other examples are described below. FIG. 9 illustrates another display example on the training monitor 138.

A deflection index 440 includes a circular arc and edges at both ends of the circular arc. The permissible deflection range is a range of the circular arc between the edges at both ends. While the end point 330b of the body core line 330 is present on the circular arc, the trainee 900 can recognize that the body core tilt falls within the permissible range. To employ a simpler deflection index, the deflection index may have only the edges indicating both ends of the permissible deflection range without rendering the circular arc.

Figure 10:
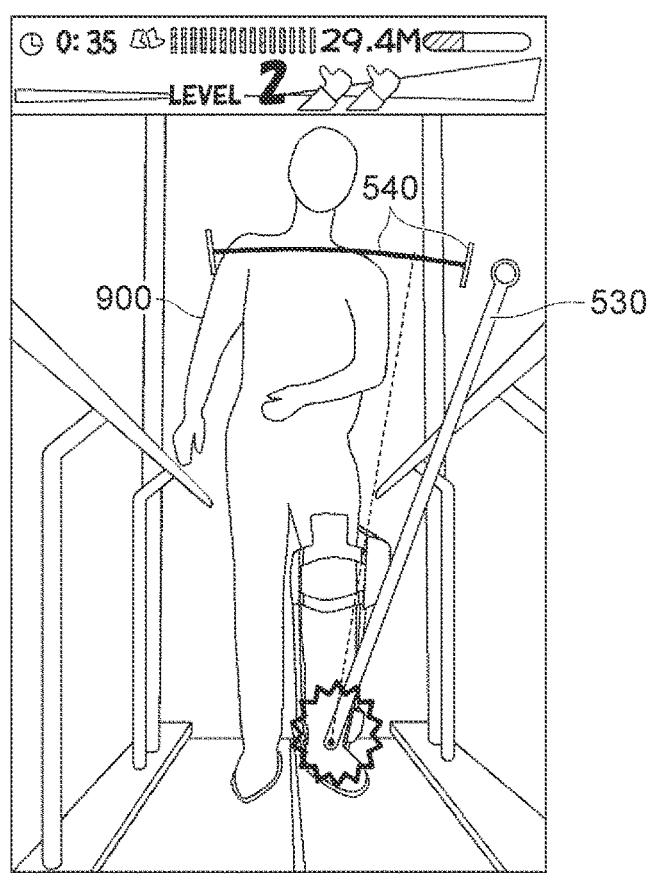
FIG. 10 is an illustration of still another display example.

FIG. 10 illustrates still another display example on the training monitor 138. A deflection index 540 is similar to the deflection index 440 illustrated in FIG. 9 in terms of the structure of the deflection index. In this case, a body core line 530 that swings at an angle twice as large as an actual deflection angle is employed. Along with this, the permissible deflection range of the deflection index 540 is rendered at a double length. Thus, the body core line 330 tilts by an amount larger than that of an actual body core tilt (tilt represented by a dashed line). Therefore, the trainee 900 can recognize his/her body core tilt more responsively. The increase factor is not limited to 2. For example, the increase factor may be selectable as appropriate depending on the phase of training. The above display format may be selected in a phase in which the training proceeds and the body core tilt decreases. When the body core significantly tilts in an initial phase of training, the body core line 530 may be swung at an increase factor smaller than 1, and the permissible deflection range of the deflection index 540 may be rendered narrower along with the swing.

In the embodiment described above, the body core line is rendered as the CG image of the straight pole, but may be rendered in any way as long as an angle associated with a body core tilt is recognized. The base point of the body core line is defined near the heel of the affected leg, but is not limited to this case. For example, the base point may be rendered in association with leg motion so that the base point is defined on a foot in contact with the ground. In this embodiment, description is given of the body core tilt in the case where the trainee 900 is observed from the front. The camera unit 140 may be installed so as to image the trainee 900 from the side, and a body core tilt in a front-rear direction of leg motion may be displayed similarly. Alternatively, body core tilts observed from the front and side may be evaluated in parallel, and videos from the front and side may be displayed alternately or in split screens.

In the embodiment described above, the body core line and the deflection index are superimposed on the image of the trainee 900 photographed by the camera unit 140, but may be displayed, for example, in different windows without superimposition. For example, the body of the trainee may be converted into a CG character and displayed as an animation without displaying the trainee image directly. Some trainees may wish to avoid observing his/her body. Therefore, it is appropriate that various display methods may be selectable.

In the walking training system, all the functional elements are not necessarily integrated into the walking training apparatus 100. For example, the function of the body core calculation unit 210a may be provided in a calculation unit of a server connected to the walking training apparatus 100 via a network. In this case, the server transmits a calculated body core tilt to the walking training apparatus 100. The overall control unit 210 of the walking training apparatus 100 achieves display similar to that of the embodiment described above by using the transmitted body core tilt. Thus, the walking training system may include the server and the walking training apparatus 100.

What is claimed is:

1. A walking training system comprising:
a treadmill configured to prompt a trainee to walk;
a display device installed such that the trainee views the display device while walking on the treadmill;
a camera configured to image the trainee at an angle at which a gait of the trainee is in view;
a calculator configured to calculate a tilt of a body core of the walking trainee based on an image captured by the camera; and
a display controller configured to control the display device to display a body core line associated with the tilt, and an index indicating at least an end of a permissible range of a deflection of the body core line,
wherein the display controller is configured to render the body core line with a base point being defined near a heel of an affected leg of the trainee.

2. The walking training system according to claim 1, wherein the display controller is configured to cause the display device to display the body core line and the index such that the body core line and the index are superimposed on the image.

3. The waking training system according to claim 1, wherein the display controller is configured to render and display the range as a sector having a pivot at the base point.

4. The walking training system according to claim 3, further comprising an evaluator configured to evaluate the gait,
wherein the display controller is configured to display an object based on an evaluation result from the evaluator.

5. The walking training system according to claim 4, wherein the display controller is configured to display an indicator serving as the object included in the sector such that the indicator increases or decreases based on the evaluator.

6. The walking training system according to claim 5, wherein the display controller is configured to display an event indicating that a level is cleared when the indicator is displayed in a full amount.

7. The walking training system according to claim 4, wherein the display controller is configured such that, when the evaluator detects inappropriateness of the gait, the object indicating the inappropriateness is displayed near the base point.

8. A non-transitory storage medium storing a control program for a walking training system including a treadmill configured to prompt a trainee to walk, a display device installed such that the trainee views the display device while walking on the treadmill, and a camera configured to image the trainee at an angle at which a gait of the trainee is in view, the non-transitory storage medium storing instructions that are executable by one or more processors and that cause the one or more processors to perform functions comprising:
calculating a tilt of a body core of the walking trainee based on an image captured by the camera; and
causing the display device to display a body core line associated with the tilt, and an index indicating at least an end of a permissible range of a deflection of the body core line,
wherein the body core line is rendered with a base point being defined near a heel of an affected leg of the trainee.

9. A control method for a walking training system including a treadmill configured to prompt a trainee to walk, a display device installed such that the trainee views the display device while walking on the treadmill, and a camera configured to image the trainee at an angle at which a gait of the trainee is in view, the control method comprising:
calculating a tilt of a body core of the walking trainee based on an image captured by the camera; and
causing the display device to display a body core line associated with the tilt, and an index indicating at least an end of a permissible range of a deflection of the body core line,
wherein the body core line is rendered with a base point being defined near a heel of an affected leg of the trainee.

* * * * *